(12) United States Patent
Crook et al.

(10) Patent No.: US 12,558,553 B2
(45) Date of Patent: Feb. 24, 2026

(54) METHOD OF PRODUCING AN IMPLANTABLE MEDICAL DEVICE

(71) Applicant: Pacesetter, Inc., Sylmar, CA (US)

(72) Inventors: Jeffery Crook, Belmont, CA (US);
Perry Li, Arcadia, CA (US)

(73) Assignee: Pacesetter, Inc., Sylmar, CA (US)

( * ) Notice: Subject to any disclaimer, the term of this patent is extended or adjusted under 35 U.S.C. 154(b) by 535 days.

(21) Appl. No.: 17/648,387

(22) Filed: Jan. 19, 2022

(65) Prior Publication Data
US 2023/0226362 A1 Jul. 20, 2023

(51) Int. Cl.
| | |
|---|---|
| *A61N 1/375* | (2006.01) |
| *A61B 5/00* | (2006.01) |
| *A61N 1/372* | (2006.01) |
| *B33Y 10/00* | (2015.01) |

(52) U.S. Cl.
CPC ........ *A61N 1/37229* (2013.01); *A61B 5/0031* (2013.01); *A61N 1/375* (2013.01); *A61N 1/37512* (2017.08); *B33Y 10/00* (2014.12)

(58) Field of Classification Search
CPC ................ A61N 1/37229; A61N 1/375; A61N 1/37512; A61B 5/0031
See application file for complete search history.

(56) References Cited

U.S. PATENT DOCUMENTS

| | | | | |
|---|---|---|---|---|
| 2007/0260294 A1* | 11/2007 | Schulman | .......... | A61N 1/37229 607/60 |
| 2010/0161002 A1* | 6/2010 | Aghassian | ............... | H01Q 1/22 607/60 |
| 2016/0344094 A1* | 11/2016 | Singh | ........................ | H05B 6/06 |
| 2020/0001095 A1* | 1/2020 | Iyer | .................... | A61N 1/37229 |
| 2020/0254246 A1* | 8/2020 | Zorman | ............. | A61N 1/36007 |
| 2021/0252295 A1* | 8/2021 | English | .............. | A61N 1/37512 |
| 2022/0176132 A1* | 6/2022 | Pflug | ...................... | A61N 1/375 |
| 2023/0091809 A1* | 3/2023 | Lee | .................... | A61N 1/36038 |

OTHER PUBLICATIONS

Speciality Coating Systems, Inc., SCS Parylene Properties, 2007, pp. 1-12 (Year: 2007).*
Olmos et al., Thermo-mechanical properties of polysulfone based nanocomposites with well dispersed silica nanoparticles, 2014, pp. 307-314 (Year: 2014).*

* cited by examiner

*Primary Examiner* — Catherine M Voorhees
(74) *Attorney, Agent, or Firm* — Dean D. Small; Carroll, Hoette & Butscher, LLC

(57) ABSTRACT

A method for producing an implantable medical device (IMD) includes forming a channel along a surface of a housing of the IMD, and depositing a conductive material into the channel to at least partially fill the channel and form an antenna of the IMD on the housing. The method also includes electrically connecting the antenna to communication circuitry contained within the housing to facilitate wireless communication with at least one of a second IMD or an external device.

16 Claims, 7 Drawing Sheets

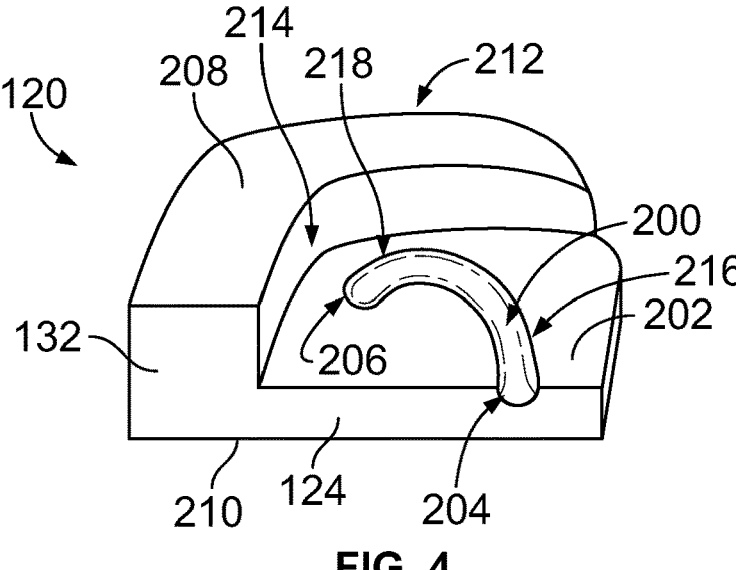
FIG. 4
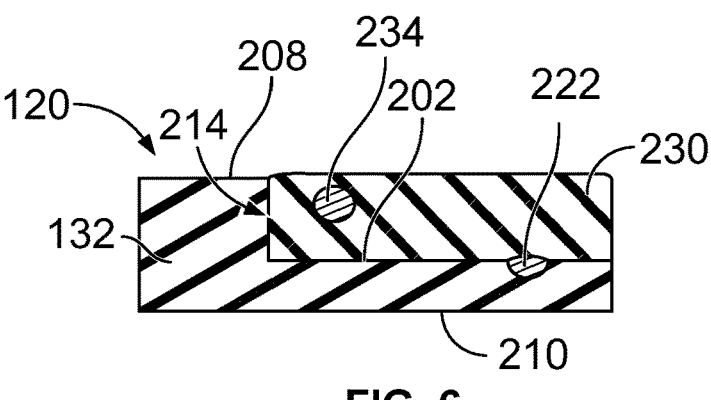
FIG. 5
FIG. 6

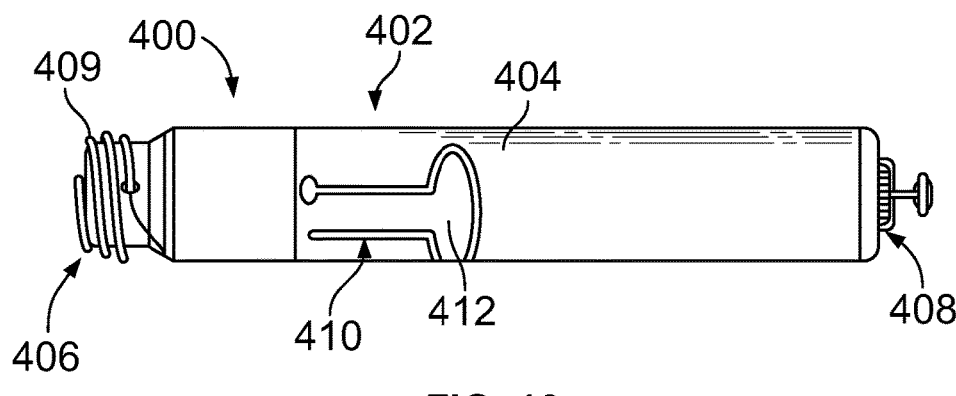
FIG. 10
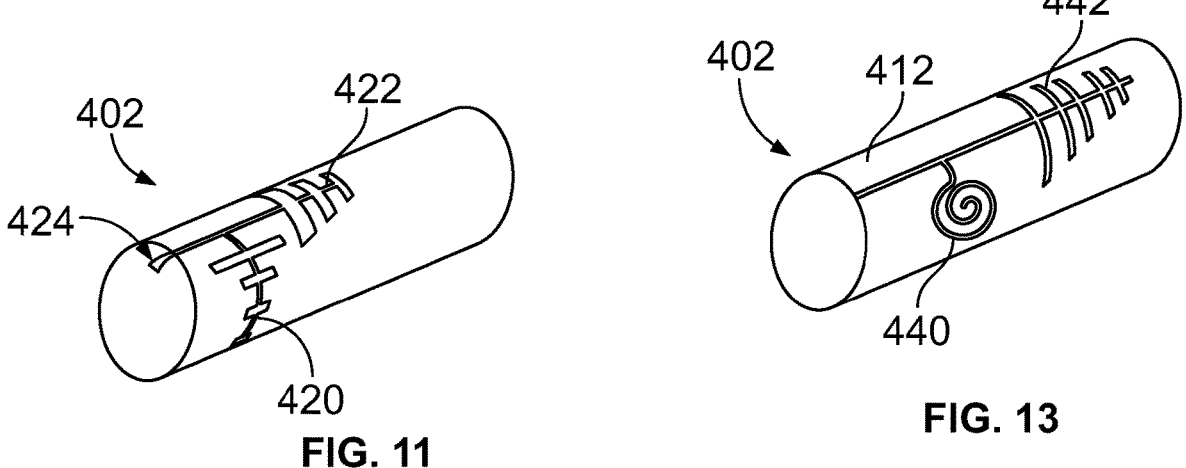
FIG. 11
FIG. 13
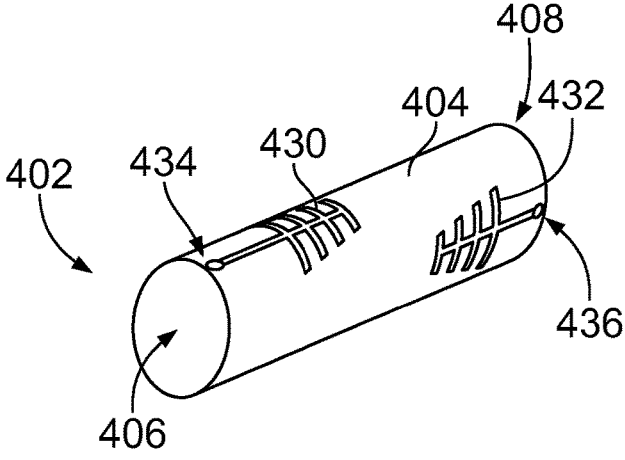
FIG. 12

600

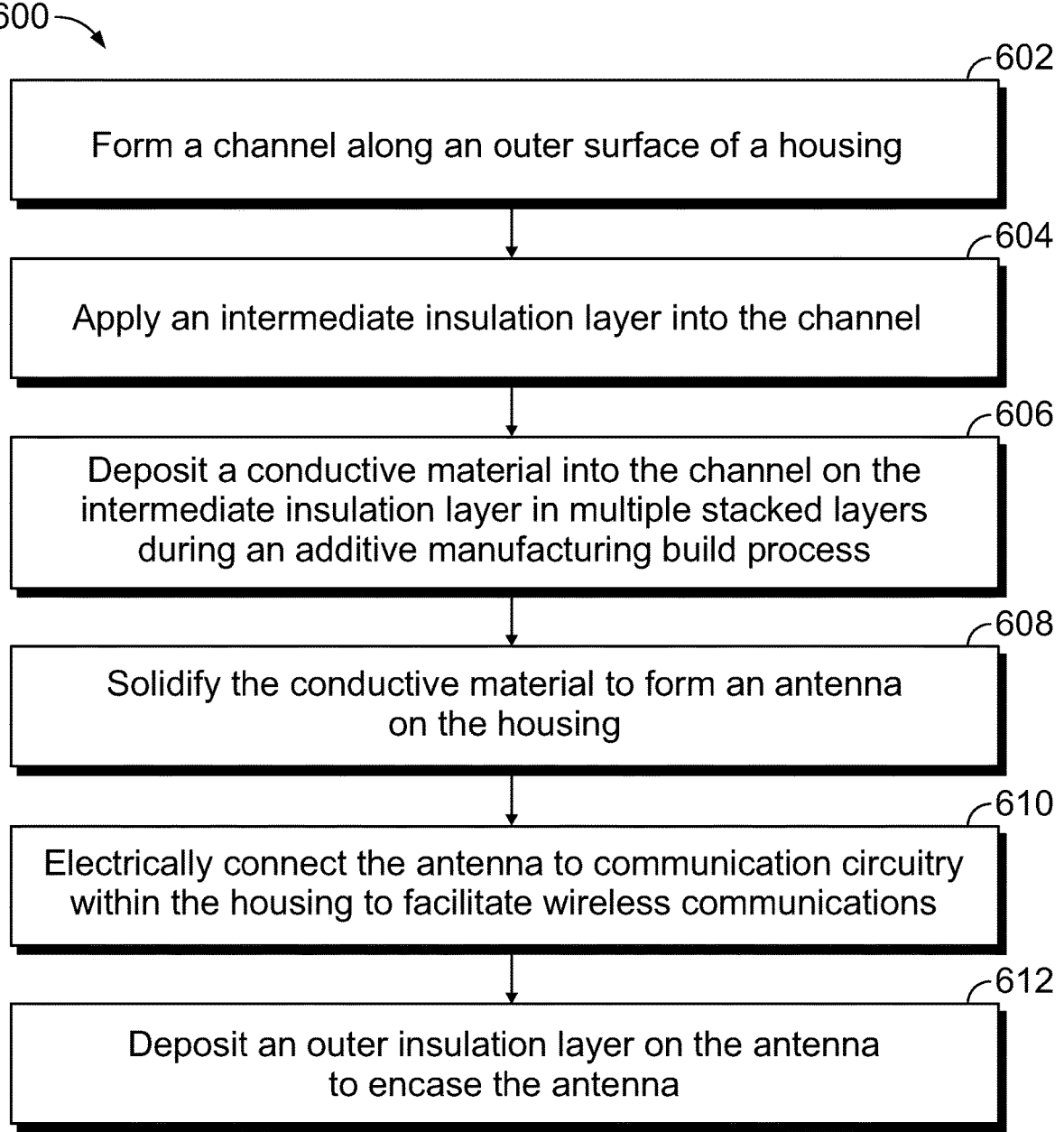

602

Form a channel along an outer surface of a housing

604

Apply an intermediate insulation layer into the channel

606

Deposit a conductive material into the channel on the intermediate insulation layer in multiple stacked layers during an additive manufacturing build process

608

Solidify the conductive material to form an antenna on the housing

610

Electrically connect the antenna to communication circuitry within the housing to facilitate wireless communications

612

Deposit an outer insulation layer on the antenna to encase the antenna

FIG. 15

METHOD OF PRODUCING AN IMPLANTABLE MEDICAL DEVICE

BACKGROUND

Embodiments of the present disclosure generally relate to implantable medical devices (IMDs) and methods of producing the IMDs, and more particularly to methods of forming communication antennas of the IMDs.

Various types of implantable devices are utilized today for monitoring physiologic activity of a patient and potentially delivering therapy to the patient. Example types of IMDs include pacemakers, implantable cardioverter defibrillators, implantable cardiac monitors, implantable neurostimulator devices, and cardiac rhythm management devices. Some IMDs include at least one antenna for wireless communications with another device, such as a second IMD within the patient's body or an external device outside of the patient's body. The antennas used in known IMDs are discrete metal elements, such as sheet metal that is stamped and formed to adopt a non-planar shape. The pre-formed antenna is loaded into a cavity of a housing of the IMD, and then the antenna is welded to one or more corresponding conductive elements to electrically connect the antenna to communication circuitry of the IMD.

With the increased miniaturization of IMDs, this conventional assembly technique for attaching the antennas to the IMDs becomes more challenging. For example, as the size of the antenna decreases, the steps of forming the antenna, loading the antenna in place on the housing, and welding the antenna to the corresponding conductive elements become more difficult. Another challenge associated with miniaturization of the IMDs is avoiding diminished wireless communication, such as a reduction in antenna gain and/or signal strength.

A need remains for a method of providing one or more antennas on an IMD with less complexity than the conventional approach and an enhanced ability to accommodate a small form factor of the IMD, without sacrificing antenna performance.

SUMMARY

In one or more embodiments, a method for producing an implantable medical device (IMD) is provided that includes forming a channel along a surface of a housing of the IMD, and depositing a conductive material into the channel to at least partially fill the channel and form an antenna of the IMD on the housing. The method also includes electrically connecting the antenna to communication circuitry contained within the housing to facilitate wireless communication with at least one of a second IMD or an external device.

Optionally, the conductive material may be deposited into the channel in multiple stacked layers during an additive manufacturing build process. The conductive material may be deposited into the channel while the conductive material in a non-solid state and may conform to a shape of the channel. The conductive material may form the antenna in-situ on the housing upon solidifying.

Optionally, the method includes positioning a pin for a tip of the pin to extend into a connection end of the channel and contact the conductive material of the antenna. The pin may be electrically connected to communication circuitry within the housing.

Optionally, the method includes depositing an electrically insulative material on the surface of the housing to encase the antenna.

Optionally, the method includes submitting the housing to a heat application after depositing the conductive material to harden the conductive material and form the antenna.

Optionally, the housing includes a header and a main body that contains a battery and an electronics module. The method may include attaching the header to an end of the main body. Forming the channel along the surface of the housing may include forming the channel along an outer surface of the main body.

Optionally, the housing includes a main body that is electrically conductive. The method may include applying an intermediate insulation layer that surrounds the main body prior to depositing the conductive material into the channel such that the intermediate insulation layer is disposed between the conductive material and the main body. The method may also include applying an outer insulation layer that surrounds the conductive material and the intermediate insulation layer to encase the antenna.

Optionally, the housing includes a cylindrical body and the channel is formed along an outer surface of the cylindrical body such that the antenna formed within the channel curves along at least one-fourth of a circumference of the cylindrical body. Optionally, forming the channel along the surface of the housing comprises forming a primary portion and multiple secondary portions that branch off from the primary portion of the channel.

Optionally, the channel is a first channel, the antenna is a first antenna, and the method also includes forming a second channel along the surface of the housing, and depositing the conductive material into the second channel to at least partially fill the second channel and form a second antenna of the IMD on the housing. The second channel has one of (i) a different shape than the first channel along the surface of the housing for the second antenna to provide different antenna properties than the first antenna, or (ii) a same shape as the first channel and is at least one of spaced apart from the first channel along a dimension of the housing or oriented to project in a different direction than the first channel.

In one or more embodiments, an implantable medical device is provided that includes a housing, a pin, and an antenna. The housing contains a battery and an electronics module. The housing defines a channel along an outer surface of the housing. The channel extends from a connection hole. The pin is electrically connected to communication circuitry of the electronics module. A tip of the pin is positioned at the connection hole. The antenna is disposed within the channel along the outer surface of the housing. The antenna is electrically connected to the pin and configured to facilitate wireless communication with and at least one of a second IMD or an external device.

Optionally, the tip of the pin is embedded within a conductive material of the antenna. Optionally, the implantable medical device includes an outer insulation layer that encases the antenna. Optionally, a body of the housing that defines the outer surface is electrically conductive, and an intermediate insulation layer is disposed between the antenna and the body to electrically insulate the antenna from the body.

Optionally, the channel defined along the outer surface of the housing has a primary portion and multiple secondary portions that branch off from the primary portion of the channel. Optionally, the housing includes a cylindrical body that defines the channel, and the antenna within the channel curves along at least one-fourth of a circumference of the cylindrical body.

In one or more embodiments, a method for producing an IMD is provided. The method includes forming a channel along an outer surface of a housing of the IMD. The outer surface of the housing is electrically conductive. The method includes applying an intermediate insulation layer on the surface of the housing and within the channel, and depositing a conductive material that is in a non-solid state into the channel to at least partially fill the channel. The conductive material forms an antenna of the IMD on the housing upon the conductive material solidifying. The method includes electrically connecting the antenna to communication circuitry contained within the housing for the antenna to facilitate wireless communication for the IMD. The method includes applying an outer insulation layer that covers the antenna to encase the antenna between the outer insulation layer and the intermediate insulation layer.

Optionally, the conductive material is deposited into the channel in multiple stacked layers during an additive manufacturing build process. Optionally, forming the channel along the outer surface of the housing includes forming a primary portion of the channel and multiple secondary portions of the channel that branch off from the primary portion.

BRIEF DESCRIPTION OF THE DRAWINGS

FIG. 4 illustrates a header of a housing of the IMD at a first stage of an assembly process according to an embodiment.

FIG. 5 illustrates the header at a second stage of the assembly process according to an embodiment.

FIG. 6 is a cross-sectional view of the header at a third stage of the assembly process according to an embodiment.

FIG. 10 is a perspective view of a housing of an IMD according to another embodiment.

FIG. 11 shows the housing of FIG. 10 including a first antenna and a second antenna according to a first multi-antenna embodiment.

FIG. 12 shows the housing of FIG. 10 including a first antenna and a second antenna according to a second multi-antenna embodiment.

FIG. 13 shows the housing of FIG. 10 including a first antenna and a second antenna according to a third multi-antenna embodiment.

FIG. 15 is a flow chart of a method for producing an IMD according to another embodiment.

DETAILED DESCRIPTION

Figure 1:
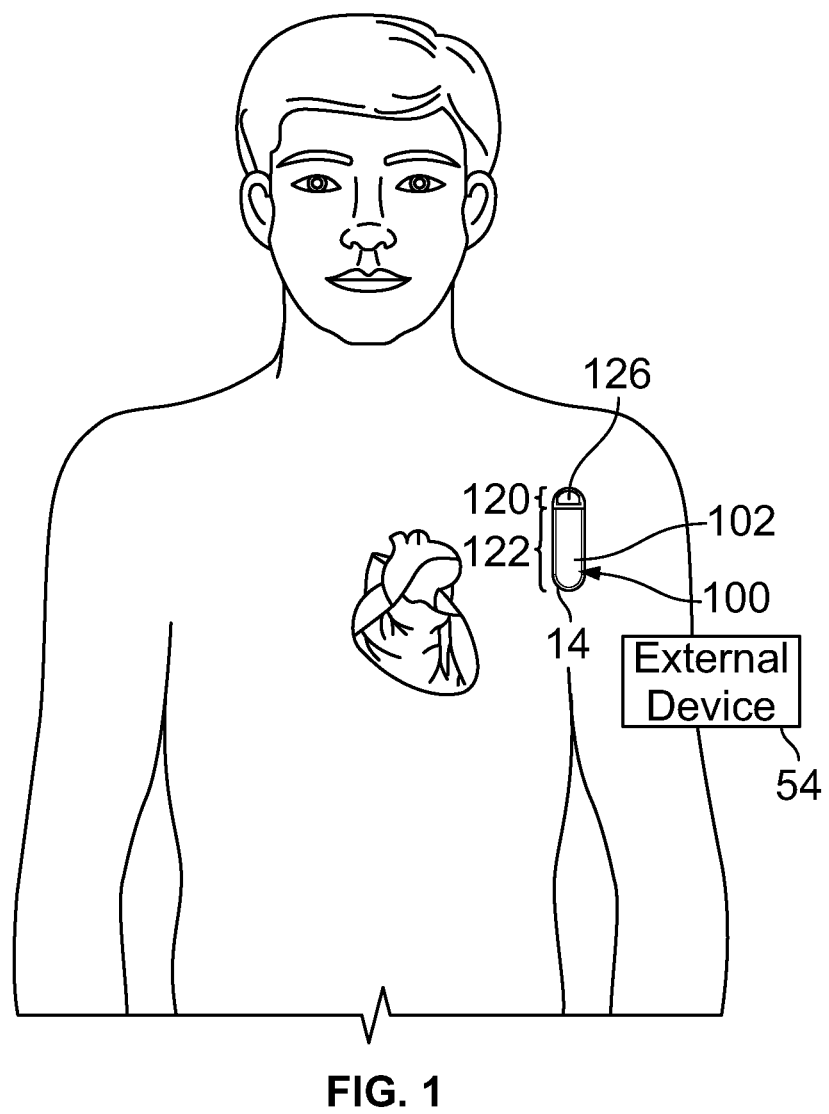
FIG. 1 illustrates an implantable medical device (IMD) intended for subcutaneous implantation at a site near the heart.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

The term "additive manufacturing" as used herein refers to a build process for constructing three-dimensional (3D) structures layer by layer in a stacked arrangement. Additive manufacturing is also known as 3D printing. Suitable processes include, for example, material extrusion, material jetting, and binder jetting.

The term "in-situ" is used herein with reference to formation of antennas and indicates that the antenna has not been moved from its original place of formation. Antenna formation in-situ on a housing indicates that the antenna was not formed elsewhere and then attached to the housing, but rather was constructed from its base material on the housing itself. For example, the base material is deposited or applied to the housing in a non-antenna shape and/or consistency, and the base material assumes the antenna shape and consistency while on the housing.

The term "leadless" generally refers to an absence of electrically-conductive leads that traverse vessels or other anatomy outside of the intra-cardiac space, while "intra-cardiac" means generally, entirely within the heart and associated vessels, such as the superior vena cava (SVC), inferior vena cava (IVC), coronary sinus (CS), coronary veins (CV), pulmonary arteries, and the like.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

Embodiments may be implemented in connection with one or more implantable medical devices (IMDs). Non-limiting examples of IMDs include neurostimulator devices, implantable leadless monitoring and/or therapy devices, and alternative implantable medical devices. For example, an IMD may represent a cardiac monitoring device, a leadless pacemaker, a cardioverter, a cardiac rhythm management device, a defibrillator, a neurostimulator, or the like.

FIG. 1 illustrates an implantable medical device (IMD) 100 intended for subcutaneous implantation at a site near the heart. The IMD 100 may provide comprehensive safe diagnostic data reports including a summary of heart rate, in order to assist physicians in diagnosis and treatment of patient conditions. By way of example, reports may include episodal diagnostics for auto trigger events, episode duration, episode count, episode date/time stamp and heart rate histograms. The IMD 100 may be configured to be relatively small (e.g., between 2-10 cc in volume) which may, among other things, reduce risk of infection during implant procedure, afford the use of a small incision, afford the use of a smaller subcutaneous pocket and the like. The small footprint may also reduce implant time and introduce less change in body image for patients.

The IMD 100 provides a data storage option that is simple to configure to enable physicians to prioritize data based on individual patient conditions, to capture significant events and reduce risk that unexpected events are missed. The IMD 100 may have programmable pre- and post-trigger event storage. For example, the IMD 100 may be automatically activated to store 10-60 seconds of activity data prior to an event of interest and/or to store 10-60 seconds of post event activity. Optionally, the IMD 100 may afford patient triggered activation in which pre-event activity data is stored, as well as post event activity data (e.g., pre-event storage of 1-105 minutes and post-event storage of 30-60 seconds). Optionally, the IMD 100 may afford manual (patient triggered) or automatic activation for EGM storage. Optionally, the IMD 100 may afford additional programming options (e.g., asystole duration, bradycardia rate, tachycardia rate, tachycardia cycle count). The amount of EGM storage may vary based upon the size of the memory.

The IMD 100 includes a housing 102. The housing 102 in the illustrated embodiment has a small form factor with an elongated shape. The housing 102 has curved ends and rounded or beveled edges to avoid snagging and/or damaging tissue during implantation and extraction relative to the subcutaneous pocket of the patient. The housing 102 may include a header 120 that is attached to a main body 122. The header 120 includes at least one electrode 126 and at least one antenna. The electrode 126 may be exposed to the tissue of the patient for direct sensing of electrical signals from the tissue and/or direct emission of electrical pulses into the tissue. The main body 122 may include one or more electrodes 14 that are spaced apart from the header 120 and the electrode 126. The electrode(s) 14 may be located in various locations on the housing 102. Numerous configurations of electrode arrangements are possible. Optionally, the main body 122 itself may be electrically conductive and may represent the electrode 14.

In an embodiment, the IMD 100 senses far field, subcutaneous electrograms, processes the electrograms to detect arrhythmias and automatically records the electrograms in memory for subsequent transmission through an antenna to an external device 54. Electrogram processing and arrhythmia detection is provided for, at least in part, by algorithms embodied in the microprocessor. In one configuration, the IMD 100 is a monitoring device operative to detect atrial fibrillation (AF).

The IMD 100 in the illustrated embodiment is leadless, such that no conductive leads extend from the housing 102 to cardiac tissue within or surrounding the heart of the patient. In an alternative embodiment, the IMD 100 may include one or more leads that connect to the header 120. Each lead includes one or more electrodes along the length of the respective lead. One or more of the electrodes of the leads may be utilized to define a stimulation vector or sensing vector, instead of an electrode on the header 120. For example, the header 120 may lack the electrode 126 in the alternative embodiment with leads.

Figure 2:
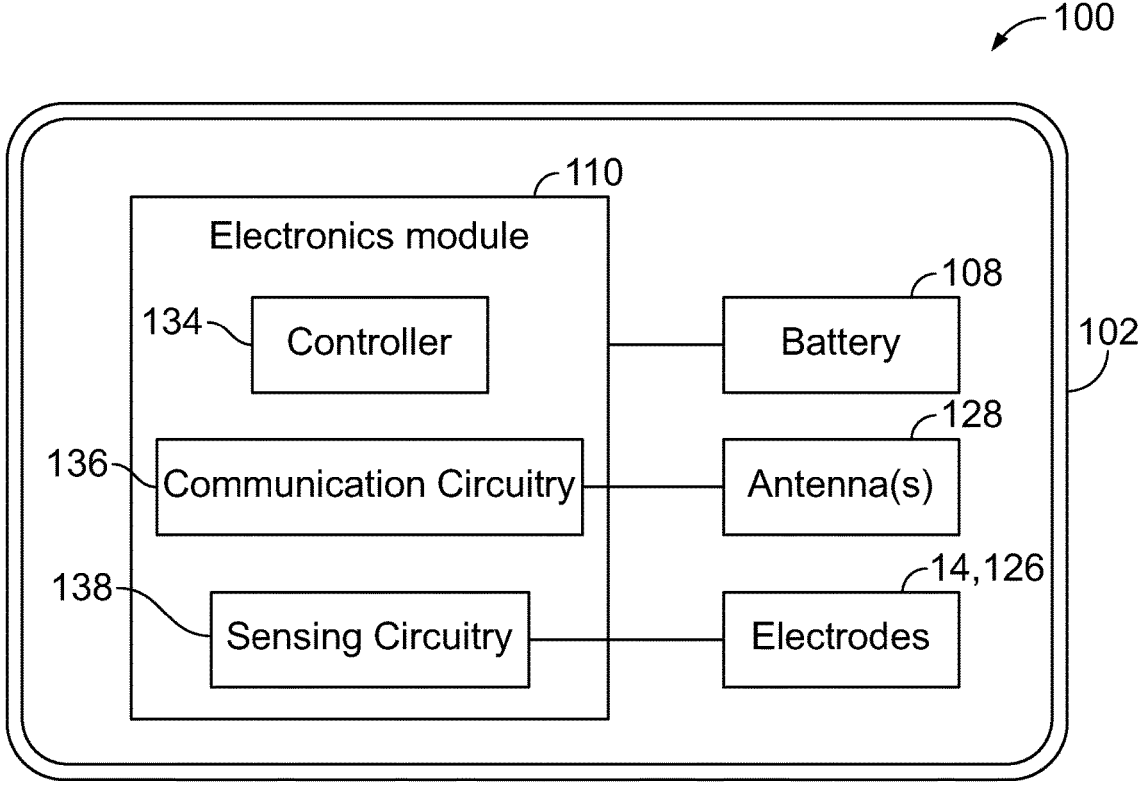
FIG. 2 is a schematic block diagram of the IMD according to an embodiment.

FIG. 2 is a schematic block diagram of the IMD 100 according to an embodiment. The IMD 100 includes an electronics module 110, a battery 108, at least one antenna 128, and the electrodes 14, 126. These components may be held within and/or on the housing 102. The battery 108 provides operating power to the components of the IMD 100. The battery 108 may be designed to operate at low current drains for long periods of time. Optionally, the battery 108 may be a secondary battery that is rechargeable via inductive coupling to a power supply external of the patient body.

The electronics module 110 may include a controller 134, communication circuitry 136, and sensing circuitry 138. The controller 134 controls various operations of the IMD 100, including cardiac monitoring. In an embodiment in which the IMD 100 includes pulse generation circuitry, the controller 134 may also control stimulation therapy. The controller 134 includes a microprocessor (or equivalent control circuitry), RAM and/or ROM memory, logic and timing circuitry, state machine circuitry, and/or I/O circuitry. The communication circuitry 136 is electrically connected to the antenna(s) 128 and enables wireless communication with the external device 54 and/or another IMD within the patient. The communication circuitry 136 may include a transceiver, or a receiver and separate transmitter. The sensing circuitry 138 is electrically connected to the electrodes 14, 126, and receives cardiac signals from the electrodes 14, 126. The sensing circuitry 138 may include dedicated sense amplifiers, multiplexed amplifiers, or shared amplifiers. At least one amplifier may be a low power, precision amplifier with programmable gain and/or automatic gain control, bandpass filtering, and threshold detection circuit to selectively sense a cardiac signal of interest.

In an embodiment, the sensing circuitry 138 receives cardiac signals (e.g., electrograms) from at least one of the electrodes 14, 126. The output of the sensing circuitry 138 is conveyed to the controller 134, which processes the received cardiac signals in accordance with one or more algorithms (e.g., an AF detection algorithm). The controller 134 may generate a control signal for the communication circuitry 136 and antenna(s) 128 to wirelessly communicate a message to an external device 54 or another IMD within the patient. The message may include the output of the one or more algorithms, such as whether the controller 134 detects that the patient is experiencing AFT. The message may include other information, such as a record of the cardiac signals received by the sensing circuitry, monitored parameters of the patient, and/or the like.

In an alternative embodiment, the electronics module 110 may include pulse generation circuitry for generating pacing pulses and/or shocking pulses to stimulate and/or modify conduction of the patient's heart. The pacing pulses and/or shocking pulses may be emitted by one or more electrodes, such as electrodes on a lead or the electrodes 14, 126 along the housing 102.

Figure 3:
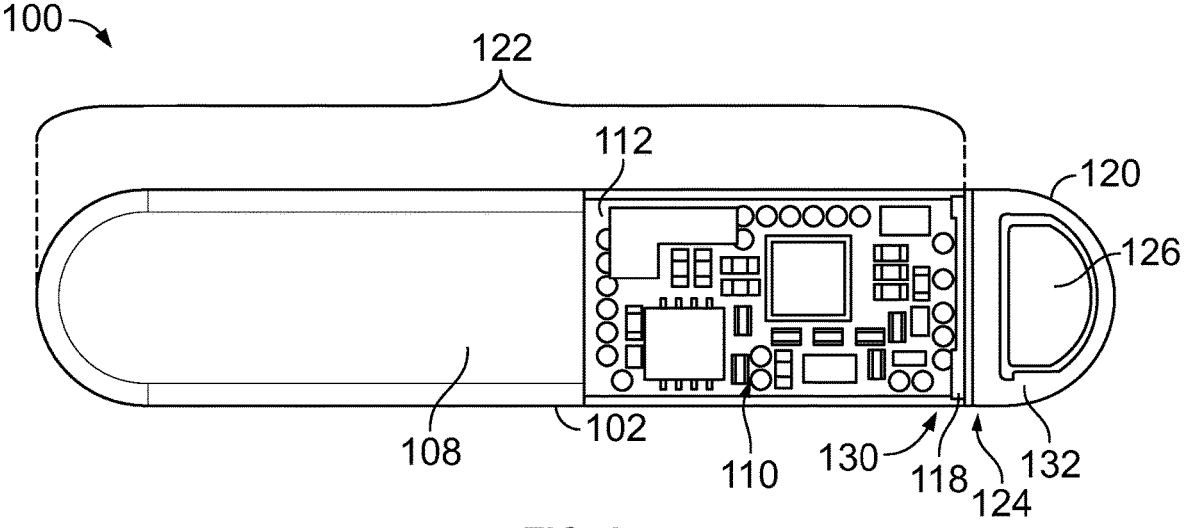
FIG. 3 illustrates a plan view of the IMD according to an embodiment.

FIG. 3 illustrates a plan view of the IMD 100 according to an embodiment. In the illustrated embodiment, the header 120 is mounted to a header end 130 of the main body 122 via a feedthrough assembly 118. The main body 122 may contain the battery 108 and the electronics module 110. The main body 122 may include top and bottom case portions, or shells, that join with one another to enclose the battery 108 and electronics module 110. One of the case portions is omitted or transparent in FIG. 2 to show the battery 108 and the electronics module 110 within an internal cavity of the main body 122. The electronics module 110 may include a circuit board 112 on which is disposed electronic circuit elements that represent the components of the electronics module 110, such as the controller 134, the communication circuitry 136, and the sensing circuitry 138.

In the illustrated embodiment, the header 120 includes a header body 132 that is formed of a generally homogeneous dielectric (e.g., electrically insulative) material. The antenna 128 shown in FIG. 2 may be disposed within an interior volume of the header body 132. For example, the antenna 128 may be behind the electrode 126 according to the orientation of the IMD 100 and the viewing angle shown in FIG. 3.

The header 120 has a mounting end 124 configured to be mounted to the feedthrough assembly 118. The sensing electrode 126 and the antenna 128 of the header 120 are electrically connected to the electronics module 110 via corresponding electrically conductive elements that project across the mounting end 124. The electrically conductive elements may include wires, traces, pins, receptacle connectors, plug connectors, and/or the like. At least some of the conductive elements may traverse the feedthrough assembly 118 at the interface between the header 120 and the main body 122. In an alternative embodiment, the IMD 100 does not have a feedthrough assembly, and the mounting end 124 of the header 120 mounts directly to the end 130 of the main body 122.

The battery 108 is electrically connected to the electronics module 110 to power the electronics module 110. The conductive elements held by the feedthrough assembly 118, such as wires, pins, or connectors, are electrically connected to corresponding circuit devices (e.g., resistors, transistors, capacitors, switch devices) of the electronics module 110. After the header 120 is mounted on the feedthrough assembly 118, the sensing electrode 126 and the antenna 128 are electrically connected to corresponding conductive elements of the feedthrough assembly 118. Once the IMD device 100 is mechanically assembled, any seams along an exterior of the housing 102 may be sealed to prevent organic fluids of the patient from leaking into the interior of the housing 102. For example, the seams may be welded, filled with a sealant, bonded, or the like to hermetically seal the IMD 100.

FIG. 4 illustrates the header 120 of the housing 102 of the IMD 100 at a first stage of an assembly process according to an embodiment. The assembly process is performed to produce (e.g., manufacture) the IMD 100. References herein to "first stage," "second stage," etc. are used to identify and distinguish between different assembly stages. The assembly may include additional stages than the stages specifically referenced as "first," "second," etc.

The header 120 includes a channel 200 that is formed along a surface 202 of the header 120. The channel 200 is an elongate, narrow groove or trough. The channel 200 extends from a connection end 204 of the channel 200 to a distal end 206 of the channel 200. In the illustrated embodiment, the connection end 204 is located at the mounting end 124 of the header 120, which attaches to the feedthrough assembly 118 or directly to the main body 122 (shown in FIG. 3). As such, the channel 200 is open to receive a pin extending from the feedthrough assembly 118 and/or the main body 122.

The surface 202 is an interior surface of the header 120. Upon completion of the header assembly process, the interior surface 202 that defines the channel 200 is within an interior volume of the header 120. For example, the header body 132 includes a first side 208 and a second side 210 opposite the first side 208. The first and second sides 208, 210 both extend from the mounting end 124 to a distal end 212 of the header 120. The header body 132 is formed to include a cavity 214 along the first side 208. The cavity 214 may be a depression or cutout region. The cavity 214 may be an integral feature of the header body 132, such that the header body 132 is molded to define the cavity 214. Alternatively, the cavity 214 may be formed by excising material of the header body 132 after the header body 132 is constructed. The cavity 214 extends a depth from the first side 208 to the interior surface 202, along which the channel 200 is formed. Optionally, the channel 200 may be integrally formed with the header body 132 in the same molding process that forms the cavity 214. Alternatively, the channel 200 may be formed by etching or scraping material from the interior surface 202, after the cavity 214 is formed along the header body 132.

The plane of the interior surface 202 (e.g., which is the plane of the channel 200) may be perpendicular to a plane of the mounting end 124 of the header 120. The channel 200 is disposed between the first side 208 and the second side 210 along the thickness of the header 120 between the first and second sides 208, 210. The channel 200 is spaced apart from both the first and second sides 208, 210. The plane of the channel 200 may be parallel or approximately parallel to the respective planes of the first and second sides 208, 210.

The channel 200 may have a shape that corresponds to an antenna design. In the illustrated embodiment, a first segment 216 of the channel 200 extends in a direction from the mounting end 124 towards the distal end 212 of the header 120, and a second segment 218 of the channel 200 curves at least partially away from the distal end 212 to resemble a hook shape. The channel 200 may have other shapes in other embodiments, such as shapes that correspond to other types of antenna designs (e.g., Yagi antenna design).

FIG. 5 illustrates the header 120 of the housing 102 of the IMD 100 at a second stage of the assembly process according to an embodiment. A conductive material 220 is deposited into the channel 200. The conductive material 220 at least partially fills the channel 200. The conductive material 220 adopts the shape of the channel 200. For example, the conductive material 220 extends to the connection end 204 and may also extend to the distal end 206 of the channel 200. In an embodiment, the conductive material 220 does not overflow the channel 200, such that the material 220 does not cover the interior surface 202 outside of the channel 200.

The conductive material 220 is electrically conductive. The conductive material 220 may be a conductive epoxy, a metal, or the like. The metal may be a pure or substantially pure metal or an alloy of multiple metals. The conductive material 220 forms an antenna 222 of the IMD 100 in-situ on the header 120. The antenna 222 facilitates wireless communication between the communication circuitry 136 of the IMD 100 and another device, such as a second IMD or an external device (e.g., external device 54 in FIG. 1).

In an embodiment, the conductive material 220 is deposited into the channel 200 while the conductive material 220 is in a non-solid state. In the non-solid state, the conductive material 220 may be at least partially flowable. The non-solid conductive material 220 may be liquid or a quasi-liquid (e.g., gel). The conductive material 220 forms the antenna 222 upon solidifying. The conductive material 220 is not injection molded on the housing 102. The conductive material 220 may be deposited into the channel 200 via an applicator 224. The applicator 224 may be a nozzle that dispenses the conductive material 220 into the channel 200. In an embodiment, the applicator 224 may be held stationary, and the conductive material 220 flows along the length of the channel 200 to at least partially fill the channel 200. In another embodiment, the applicator 224 may be a component of an additive manufacturing system. The applicator 224 may be controlled by one or more actuators to move relative to the header 120 as the applicator 224 deposits the conductive material 220. For example, the additive manufacturing system may deposit the conductive material 220 into the channel 200 in multiple layers which bond together to form the antenna 222.

The conductive material 220 engages a tip 226 of a pin 228. The pin 228 is electrically connected to the communication circuitry 136 of the electronics module 110. The method of producing the IMD 100 may include attaching the pin 228 to the housing 102 such that the pin 228 extends into the connection end 204 of the channel 200. For example, the pin 228 may be attached to the feedthrough assembly 118 and/or the main body 122. The tip 226 of the pin 228 engages and electrically connects to the conductive material 220. The conductive material 220 at the connection end 204 at least partially coats and conforms to the tip 226 such that the antenna 222 is formed in mechanical and electrical connection with the pin 228. For example, the tip 226 of the pin 228 may be positioned at the connection end 204 prior to depositing the conductive material 220 into the channel 200, while the conductive material 220 is deposited, or after the conductive material 220 is deposited and still in the non-solid state before setting (e.g., solidifying) to form the antenna 222. The tip 226 of the pin 228 may be embedded in the antenna 222 when the conductive material 220 solidifies.

In an embodiment, after the conductive material 220 is deposited into the channel 200 and is connected to the pin 228, the conductive material 220 is actively or passively controlled to solidify and set, to define the antenna 222 and secure the connection to the pin 228. For example, the conductive material 220 may be allowed to cool, either passively in a room temperature environment or actively by chilling the header 120 at a temperature below room temperature, until the conductive material 220 solidifies. Alternatively, the conductive material 220 may solidify in response to heat. In that case, the header 120 of the housing 102 may be submitted to a heat application to harden the conductive material 220. For example, the header 120 may be placed into an oven/furnace that is set to a designated temperature and retained in the oven/furnace for a designated period of time to bake or cure the conductive material 220. The designated temperature and designated period of time may be selected based on material properties of the conductive material 220.

FIG. 6 is a cross-sectional view of the header 120 at a third stage of the assembly process according to an embodiment. The cross-section is taken along line 6-6 in FIG. 5. In an embodiment, after the antenna 222 is formed in-situ on the interior surface 202 of the header 120, an electrically insulating material 230 is deposited on the interior surface 202 to encase the antenna 222. In the illustrated embodiment, the electrically insulating material 230 is a potting material that backfills the cavity 214 of the header body 132. The electrically insulating material 230 covers the antenna 222, such that the antenna 222 is surrounded by the header body 132 and the electrically insulating material 230. As a result, the antenna 222 is disposed within an inner volume of the header 120 along the thickness of the header 120 (e.g., between the first and second sides 208, 210). No portion of the antenna 222 is exposed to the organic environment within the patient when implanted. For example, the portion of the antenna 222 at the connection end 204 is disposed along the mounting end 124 of the header 120, and the mounting end 124 is not an external surface or otherwise exposed to the organic environment when the IMD 100 is fully assembled and implanted.

In an embodiment, both the electrically insulating material 230 and the header body 132 have electrically-insulating, or dielectric, properties to avoid electrically interfering with the wireless signals emitted from and/or received at the antenna 222. One or both of the material 230 or the header body 132 may be a thermoplastic elastomer, a non-conductive epoxy, silicone, or the like. The material(s) of the electrically insulating material 230 and the header body 132 may be selected to be biocompatible with the organic tissue of the patient.

Optionally, prior to depositing the electrically insulating material 230, the electrode 126 (shown in FIGS. 1 and 3) may be electrically connected to a pin 234 or other electrically conductive element. The pin 234 may be electrically connected to the sensing circuitry 138 of the electronics module 110. The electrode 126 may be welded to an end of the pin 234. The pin 234 projects beyond the mounting end 124 of the header 120, similar to the pin 228 that is electrically connected to the antenna 222. The electrically insulating material 230 may overmold at least a portion of the pin 234, such as the portion of the pin 234 shown in cross-section in FIG. 6.

The header 120 may be attached to the main body 122 either before or after depositing the electrically insulating material 230 to backfill the cavity 214. The header 120 may be bonded to the main body 122 or secured via friction fit. The interface between the header 120 and the main body 122 (e.g., at the feedthrough assembly 118) may be hermetically sealed, such as by application of a sealant, to prevent the formation of leak paths into the housing 102. The sealant may be composed of alumina, parylene, polyurethane, silicone, an epoxy material, or the like.

Figure 7:
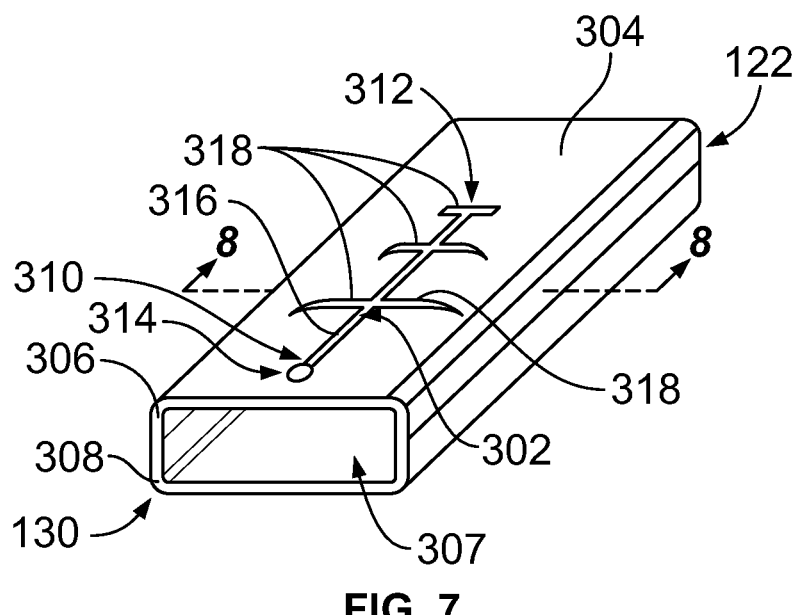
FIG. 7 illustrates a main body of the housing of the IMD at a first stage of an assembly process according to a second embodiment.

FIG. 7 illustrates the main body 122 of the housing 102 of the IMD 100 at a first stage of an assembly process according to a second embodiment. In this second embodiment, an antenna 300 (shown in FIG. 8) is formed in-situ on the main body 122 of the housing 102. For example, the header 120 may not include the antenna 222 shown in FIG. 5. The antenna 300 may be electrically connected to the communication circuitry 136 of the electronics module 110. In an alternative embodiment, the housing 102 may include both the antenna 222 that is formed on the header 120 and the antenna 300 that is formed on the main body 122.

As shown in FIG. 7, a channel 302 is formed along a surface 304 of the main body 122. The surface 304 is an outer surface of the main body 122. The outer surface 304 may be a portion of a first shell 306 of the main body 122. The first shell 306 couples to a second shell 308 to form the main body 122 and define a compartment 307 that receives the electronics module 110 and the battery 108. The outer surface 304 faces away from the compartment 307. The channel 302 may be formed while the first shell 306 is being molded, or subsequent to forming the first shell 306 via etching or the like.

The channel 302 extends from a connection end 310 of the channel 302 to a distal end 312 of the channel 302 that is opposite the connection end 310. A hole 314 through the main body 122 is located at the connection end 310 in the illustrated embodiment. The hole 314 is open (e.g., fluidly connects) to the compartment 307. A pin that is electrically connected to the communication circuitry 136 may be positioned within the compartment 307 such that a tip of the pin extends into (or at least aligns with) the hole 314 to engage conductive material (e.g., the conductive material 220) that forms the antenna 300.

The channel 302 is formed such that the shape of the channel 302 corresponds to an antenna shape. The antenna shape may be selected based on intended properties or characteristics of the antenna 300 that is to be formed, such as whether the antenna 300 will be monopole or bipolar. In the illustrated embodiment, the channel 302 has a primary portion 316 and multiple secondary portions 318 that branch off from the primary portion 316. The primary portion 316 extends the length of the channel 302 from the hole 314 to the distal end 312. The primary portion 316 may be linear. The secondary portions 318 may extend in two opposite directions from the primary portion 316 at different locations along the length of the primary portion 316. The shape of the channel 302 in the illustrated embodiment may correspond to a Yagi antenna shape. The channel 302 may have other shapes in other embodiments.

Figure 8:
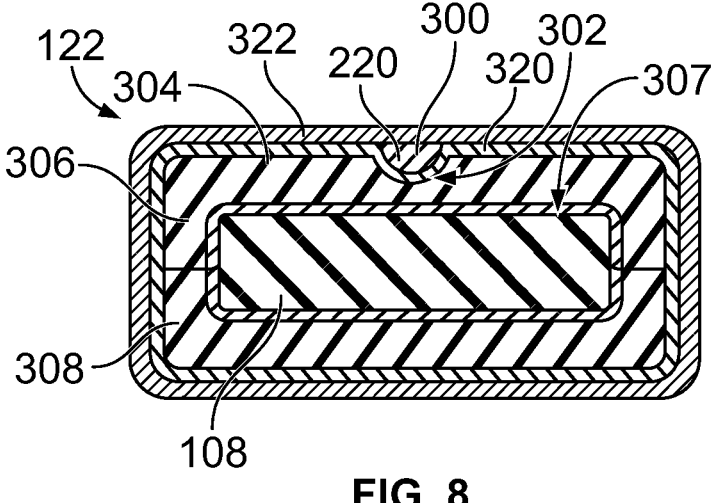
FIG. 8 is a cross-sectional view of the main body of the housing at a second stage of the assembly process according to the second embodiment shown in FIG. 7.

FIG. 8 is a cross-sectional view of the main body 122 of the housing 102 at a second stage of the assembly process according to the second embodiment shown in FIG. 7. The cross-section is taken along line 8-8 in FIG. 7. The second stage illustrated in FIG. 8 may represent a final stage of the assembly process. The electronics module 110 and the battery 108 are loaded into the compartment 307 of the main body 122, either before or after coupling the first shell 306 to the second shell 308. The cross-section extends through the battery 108 in FIG. 8.

In an embodiment, the shells 306, 308 of the main body 122 are electrically conductive. For example, the shells 306, 308 may be composed of titanium or another metal. After the main body 122 is assembled to contain the electronics module 110 and the battery 108, and the channel 302 is formed on the outer surface 304 of the first shell 306, the assembly process may include applying an intermediate insulation layer 320 that surrounds the main body 122. The intermediate insulation layer 320 may be composed of a dielectric material, such as a thermoplastic elastomer, a non-conductive epoxy, silicone, or the like. The intermediate insulation layer 320 may be coated on the outer surface 304. Optionally, the intermediate insulation layer 320 may surround an entirety of the perimeter of the main body 122. The main body 122 may be dipped into the material that forms the layer 320, or the material that forms the layer 320 may be sprayed onto the main body 122. Alternatively, the intermediate insulation layer 320 may only be located on the outer surface 304 of the first shell 306. The intermediate insulation layer 320 may be sufficiently thin to avoid filling the channel 302.

After applying the intermediate insulation layer 320, the conductive material 220 may be deposited into the channel 302 on top of the intermediate insulation layer 320. The deposition of the conductive material 220 into the channel 302 may be similar to the deposition of the conductive material 220 into the channel 200 described with reference to FIG. 5. The intermediate insulation layer 320 is disposed between the conductive material 220 and the conductive first shell 306 of the main body 122. The antenna 300 is formed from the conductive material 220, such as when the conductive material 220 solidifies. The intermediate insulation layer 320 electrically insulates the antenna 300 from the conductive main body 122.

In an embodiment, after forming the antenna 300, an outer insulation layer 322 is applied to surround the antenna 300 (e.g., the conductive material 220 thereof) and the intermediate insulation layer 320. The antenna 300 is encased between the outer insulation layer 322 and the intermediate insulation layer 320. The outer insulation layer 322 may be composed of a dielectric material that is biocompatible, such as parylene. The outer insulation layer 322 may define an exterior surface of the housing 102 that is exposed to organic tissue and fluid of the patient. Optionally, the outer insulation layer 322 may surround an entirety of the perimeter of the main body 122.

The antenna 300 is formed to have desired properties for to facilitating wireless communication with at least one of a second IMD or an external device outside of the patient. For example, that antenna 300 may be monopole or dipole, may be tuned to a desired frequency (e.g. 400 MHz, 2.4 GHz etc.), and the like. Due to the flexibility that this in-situ formation process allows, the antenna 300 can be any of various different types of antennas (e.g., monopole, patch, dipole, reflector, folded-dipole, helix, loop, inverted-F, etc.). The antenna 300 may be built onto the IMD housing without any new tooling or fixturing.

With reference back to FIGS. 4 and 5, in an alternative embodiment the header body 132 of the header 120 is electrically conductive. In that case, an intermediate insulation layer, similar to the layer 320, may be applied on the surface 202 and into the channel 200 prior to depositing the conductive material 220. The intermediate insulation layer may electrically insulate the antenna 222 from the electrically conductive header body 132.

Figure 9:
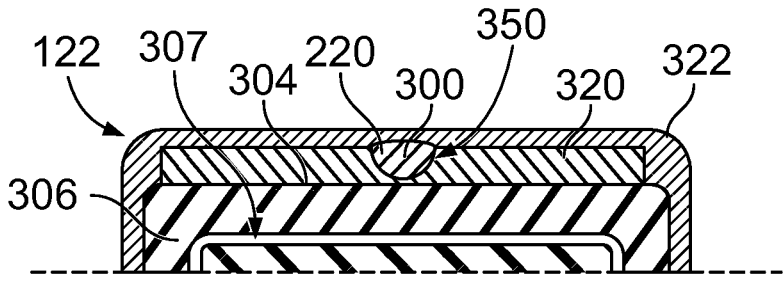
FIG. 9 is a cross-sectional view of a portion of the main body of the housing according to an alternate embodiment relative to FIGS. 7 and 8.

FIG. 9 is a cross-sectional view of a portion of the main body 122 of the housing 102 according to an alternate embodiment relative to FIGS. 7 and 8. In FIG. 9, the conductive shell 306 does not define any channel. Rather, the intermediate insulation layer 320 defines a channel 350 that extends along the outer surface 304 of the shell 306. The channel 350 extends along the outer surface 304 such that the channel 350 is proximate to the outer surface 304 and extends along a plane that is parallel to the outer surface 304. A portion of the intermediate insulation layer 320 is disposed between a base of the channel 350 and the outer surface 304. The channel 350 may have an antenna shape, such as the shape of the channel 302 shown in FIG. 7. The conductive material 220 is deposited into the channel 350 to form the antenna 300. Then, the outer insulation layer 322 is applied to cover the antenna 300, as described with reference to FIG. 8.

Optionally, as shown in FIG. 9, the intermediate insulation layer 320 does not fully surround the main body 122, but rather only extends along the outer surface 304. The outer insulation layer 322 may surround the entire perimeter of the main body 122. In an alternative embodiment, the intermediate insulation layer 320 fully surrounds the main body 122, and the outer insulation layer 322 only covers a portion of the intermediate insulation layer 320 that includes the antenna 300, without surrounding the entire main body 122.

FIG. 10 is a perspective view of a housing 402 of an IMD 400 according to another embodiment. The IMD 400 in the illustrated embodiment is a leadless IMD. The IMD 400 may represent a cardiac monitoring device, pacemaker, cardioverter, cardiac rhythm management device, defibrillator, neurostimulator, leadless monitoring device, leadless pacemaker and the like. Additionally or alternatively, the IMD 400 may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD 400 may include one or more structural and/or functional aspects of the device(s) described in U.S. Pat. No. 9,232,485 "System And Method For Selectively Communicating With An Implantable Medical Device", which are hereby incorporated by reference.

The IMD 400 is configured to be implanted entirely within a single local chamber of the heart, such as entirely and solely within the right atrium or the right ventricle. Optionally, the IMD 100 may be implanted entirely and solely within the left atrium or the left ventricle, which may require modified implant methods compared to implantation in the right atrium or the right ventricle.

The housing 402 includes a cylindrical body 404 that extends from a first end 406 to a second end 408, opposite the first end 406. Optionally, the first end 406 or the second end 408 may be fitted with a screw member (e.g., corkscrew) 409 for attaching the housing 402 to intra-cardiac tissue of the patient when implanted. The housing 402 may represent the housing 102 of the IMD 100 in FIG. 2, such that the cylindrical body 404 contains the battery 108 and the electronics module 110. The housing 402 may comprise a conductive, biocompatible, inert, and anodically safe material such as titanium, 316L stainless steel, or other similar materials.

In the illustrated embodiment, a channel 410 is formed along an outer surface 412 of the cylindrical body 404. The channel 410 in the illustrated embodiment has a folded-dipole shape, but may have other shapes/designs in other embodiments. Conductive material is deposited into the channel 410 to form an antenna in-situ on the housing 402. The antenna has the shape of the channel 410. In an embodiment, the antenna curves along at least one-fourth of the circumference of the cylindrical body 404. Optionally, the channel 410 may be formed such that the antenna curves along at least half or even the full circumference of the body 404.

FIGS. 11 through 13 represent embodiments of the housing 402 shown in FIG. 10 with multiple antennas formed along the cylindrical outer surface 412. Although these figures show multiple antennas formed in-situ on the cylindrical housing 402 of the embodiment shown in FIG. 10, it is recognized that multiple antennas may also be formed in-situ on the header 120 shown in FIGS. 1 and 3 through 6 and/or the main body 122 shown in FIGS. 1, 3, and 7 through 9. Multiple antennas may be formed on the IMD housing to improve wireless communication performance and/or provide multiple different antenna properties and/or functions relative to having only a single antenna. For example, the antennas can improve performance by providing separate directional vector capabilities, which obviates or at least reduces the correlation between the implanted orientation of the housing and the communication quality. In another example, the two or more antennas can communicate over different frequency channels (e.g. 400 MHz, 2.4 GHz etc.) from one another for conveying different types of signals.

The antennas on each housing in FIGS. 11 through 13 may be formed as described in the embodiments above, except that both the first channel and a second channel are formed along the surface of the housing. The two channels may share a common connection end, or may have different connection ends. The conductive material is deposited in each of the two channels to form a first antenna and a second antenna in-situ on the housing.

FIG. 11 shows the housing 402 including a first antenna 420 and a second antenna 422 according to a first multi-antenna embodiment. The first and second antennas 420, 422 are connected to each other and share a common connection end 424 for connecting to at least one pin that is electrically connected to the communication circuitry 136. The two antennas 420, 422 extend in different directions. For example, the first antenna 420 may be oriented perpendicular to the second antenna 422. The first antenna 420 is elongated in a circumferential direction. The second antenna 422 is elongated in a longitudinal direction. The multiple directions may improve directional emissions.

FIG. 12 shows the housing 402 including a first antenna 430 and a second antenna 432 according to a second multi-antenna embodiment. The antennas 430, 432 are spaced apart along a length of the housing 402. The first antenna 430 extends from a first connection end 434, and the second antenna 432 extends from a second connection end 436. The first connection end 434 is disposed at or proximate to the first end 406 of the cylindrical body 404, and the second connection end 436 is disposed at or proximate to the second end 408 of the cylindrical body 404. In the illustrated embodiment, the second antenna 432 is spaced apart from the first antenna 430 longitudinally along the length of the housing 402, as well as rotationally along the circumference of the housing 402. Spacing the antennas 430, 432 apart may improve wireless reception.

In each of FIGS. 11 and 12, the two antennas have approximately the same shape. The antennas may be used to provide redundancy. The redundancy may enable the control circuitry to select which one of the antennas to use for wireless communication and/or to use both antennas. For example, during a manufacturing quality review process, the performance of the common antenna may be tested. The antenna that exhibits preferred performance may be selected for use at the exclusion of the other antenna. The selection may be accomplished using switches of the communication circuitry 136. Additionally or alternatively, the selection of one or more of the antennas may be rendered at the time of implant. For example, once a device is implanted, a physician or technician may test the performance of the multiple antennas to determine which antenna provides better communications performance (e.g. better signal-to-noise ratio, less power demand, fewer dropped data packets, etc.). The physician or technician may then select the better-performing antenna for subsequent use.

FIG. 13 shows the housing 402 including a first antenna 440 and a second antenna 442 according to a third multi-antenna embodiment. In this embodiment, the first antenna 440 has a different shape than the second antenna 442, which is the direct result of the two channels along the outer surface 412 having different shapes. The different antennas 440, 442 may have different shapes to provide different antenna properties. The properties may include tuning frequencies, directionality, etc. The controller 134 may use the different antennas 440, 442 for different operations. For example, the first antenna 440 may be utilized during "sniffing" operations or to monitor for wake-up request, while the second antenna 442 is utilized for primary transfer of data packets during a communication session.

Figure 14:
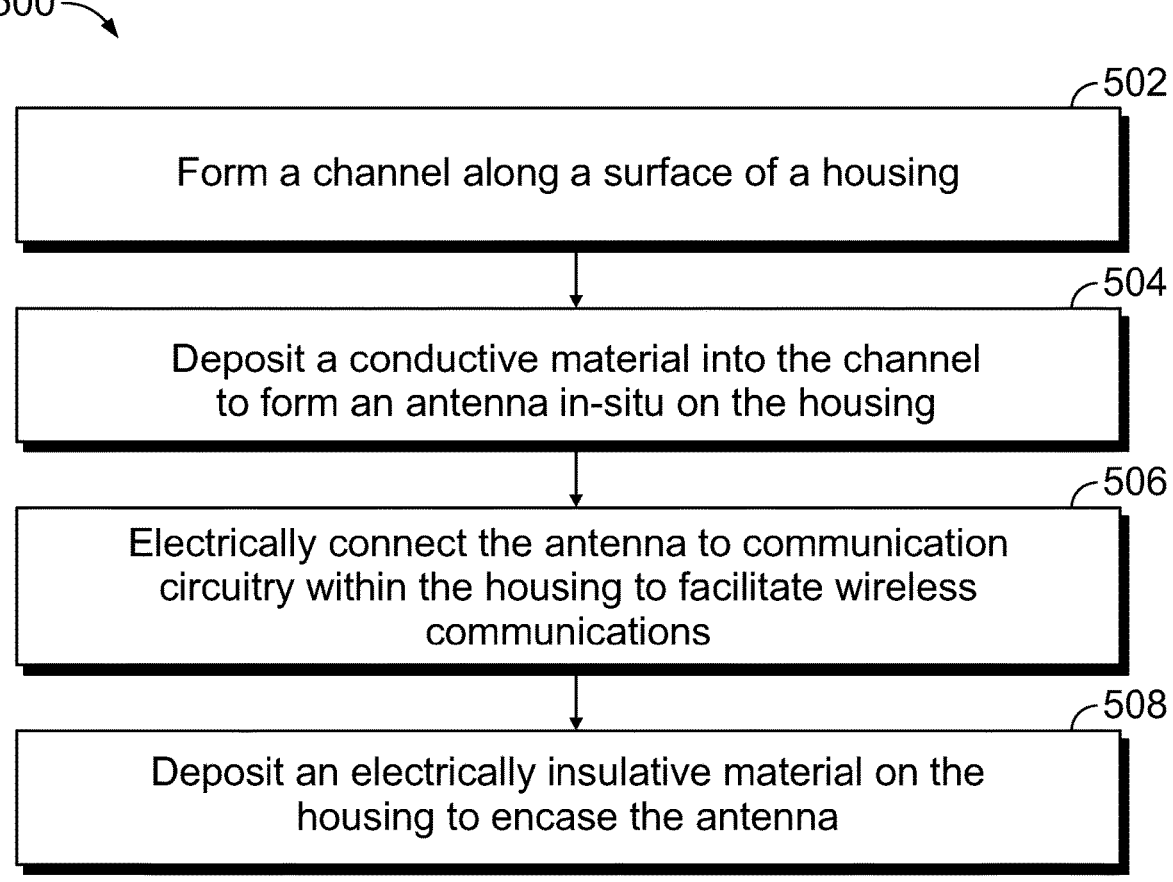
FIG. 14 is a flow chart of a method for producing an IMD according to an embodiment.

FIG. 14 is a flow chart 500 of a method for producing an implantable medical device (IMD) according to an embodiment. The method may include additional steps than shown in FIG. 14, fewer steps than shown in FIG. 14, and/or different steps than shown in FIG. 14. Furthermore, the order of the steps presented in FIG. 14 is not a limitation unless one step is specifically described as following or based on another step.

At 502, a channel is formed along a surface of a housing of an IMD. The channel is elongated and has a shape that corresponds to an antenna shape. For example, the channel may include a primary portion and multiple secondary portions that branch off from the primary portion. The channel may resemble a Yagi antenna. In an embodiment in which the housing is cylindrical, the channel may be formed to curve around at least a portion of the circumference. For example, the channel may curve along at least one-fourth of the circumference, which assist with decoupling the wireless transmission performance of the IMD from the positioning/orientation of the IMD within the patient.

In an embodiment, the channel is channel 200 that is formed along an interior surface 202 of a header 120. The header 120 attaches to a main body 122 to assemble the housing 102. In another embodiment, the channel is channel 302 that is formed along an outer surface 304 of a shell 306 of the main body 122. In yet another embodiment, the housing itself has a cylindrical body 404, and the channel 410 is formed along an outer surface 412 of the body 404.

At 504, a conductive material 220 is deposited into the channel to form an antenna in-situ on the housing. The conductive material 220 at least partially fills the channel. The conductive material 220 may be deposited while in a flowable state, such that the conductive material 220 conforms to the texture and shape of the channel. The antenna may be formed upon the conductive material 220 solidifying. For example, the conductive material 220 may have a sufficiently low viscosity to dissipate and fill the channel on its own (e.g., like a liquid). Alternatively, the conductive material 220 may be deposited by an additive manufacturing system in stacked layers within the channel. The antenna may be any of the antennas 222, 300, 420, 422, 430, 432, 440, 442 described herein.

In an embodiment in which the portion of the housing along which the channel is formed is electrically conductive, an insulative material may be applied prior to depositing the conductive material 220 to electrically insulate the conductive material 220 from the conductive portion of the housing. For example, if the shell 306 of the main body 122 is electrically conductive, the method may include coating the outer surface 304 of the shell 306 with an intermediate insulation layer 320, and then depositing the conductive material 220 within the channel 302, 350 directly on the insulation layer 320.

At 506, the antenna is electrically connected to communication circuitry 136 within the housing to facilitate wireless communications. In an embodiment, the antenna is electrically connected to a conductive pin 228 or other element that extends from the communication circuitry 136 on an electronics module 110. For example, a tip 226 of the pin 228 may be positioned at a connection end 204, 310 of the channel. The conductive material 220 may conform around the tip 226 of the pin 228 while the conductive material 220 is in the flowable state. Upon setting, the antenna 220 is physically secured to the pin 228, and is electrically connected to the communication circuitry 136 via the pin 228.

At 508, an electrically insulative material is deposited on the housing to encase the antenna. The electrically insulative material may define an exterior surface of the housing. In that case, the material may be biocompatible, such as parylene. In the embodiment in which the antenna is formed along an interior surface of a header 120, the electrically insulative material may be a backfill or potting material 230 as shown in FIG. 6. In the embodiment in which the antenna is formed along an outer surface of the housing, the electrically insulative material may be the outer insulating layer 322 shown in FIGS. 8 and 9, Optionally, the IMD may include multiple antennas on the housing that are formed via the method described herein. For example, first and second channels may be formed along the surface of the housing, or along two different surfaces of the housing. The conductive material may be deposited into each of the first and second channels to form first and second antennas in-situ on the housing. Optionally, the second channel may have a different shape than the first channel for the second antenna to have a different shape and provide different antenna properties than the first antenna. Optionally, the second channel may be spaced apart from the first channel along a dimension of the housing (e.g., longitudinal, circumferential, etc.) and/or may be oriented to project in a different direction than the first channel. As a result, the first and second antennas that are formed may provide redundancy and flexibility with respect to IMD orientation upon implant.

FIG. 15 is a flow chart 600 of a method for producing an implantable medical device (IMD) according to another embodiment. The embodiment described in the flow chart 600 may be a more specific example of the method described in the flow chart 500 of FIG. 14. At 602, a channel is formed along an outer surface of a housing of an IMD. The channel is elongated and has a shape that corresponds to an antenna shape. The housing may be cylindrical, a polygonal prism, or the like.

At 604, an intermediate insulation layer is applied into the channel. For example, the outer surface of the housing may be electrically conductive, and the intermediate insulation layer may be composed of a dielectric material, such as a thermoplastic elastomer, a non-conductive epoxy, silicone, or the like. The intermediate insulation layer defines a base layer on which the conductive material of the antenna is deposited, to avoid an electrical connection between the antenna and the conductive outer surface of the housing. The intermediate insulation layer may cover at least a portion, or even an entirety, of the outer surface surrounding the channel.

At 606, a conductive material is deposited into the channel on the intermediate insulation layer. In an embodiment, the conductive material is deposited in multiple stacked layers during an additive manufacturing build process. For example, an additive manufacturing system may apply a first layer in the channel, and then a second layer that at least partially covers first layer, etc. The additive manufacturing (e.g., 3D printing) process shapes the printable material into one or more antennas along a conductive path from the electronics modules of the IMD. Due to the flexibility that 3D printing allows, different types of antennas (e.g. Monopole, Patch, Inverted F, etc.) can be built onto the IMD without any new tooling or fixturing. The 3D printing technique is also suitable for many different IMD housing sizes and shapes. In an example, the IMD housing may be rotated while a printable material is extruded onto the housing. The intermediate insulation layer isolates the resulting antenna from the conductive housing and also adheres the antenna to the housing. The antenna may be shaped, based on the shape of the channel, to have characteristics of interest. The 3-D printing process may extract undesired portions of the printable material to leave a final antenna having a desired shape, thickness and the like. As one example, the IMD may be rotated within the 3-D printer during a printing operation to form the antenna around a curve perimeter of the IMD housing. Additionally or alternatively, when the IMD housing has flat planar sections, the IMD may be held at a temporary stationary position while the portion of the antenna is 3-D printed onto the planar housing section, as in the case of printing onto a header assembly.

At 608, the conductive material is solidified to form the antenna on the housing. The solidification step may depend on material properties of the conductive material. In an example, the housing is baked in an over or furnace at an elevated temperature to harden and solidify the conductive material. In another example, the conductive material solidifies upon cooling to room temperature, so the housing is either cooled or passively left in room temperature for a sufficient period of time to allow the temperature of the conductive material to equilibrate.

At 610, the antenna is electrically connected to communication circuitry within the housing to facilitate wireless communications. In an embodiment, the antenna is electrically connected to a conductive pin or other element that extends from the communication circuitry on the electronics module, such that the pin electrically connects the antenna to the communication circuitry. For example, a tip of the pin may be positioned at a connection end of the channel prior to depositing the conductive material. As the conductive material is deposited at step 606, the conductive material may conform around the tip of the pin while the conductive material is in the non-solid (e.g., flowable) state. Upon solidifying at step 608, the tip of the pin may be embedded within the conductive material of the antenna, which secures the pin to the antenna. In another example, the tip of the pin may be welded to the antenna after the antenna is formed on the housing.

At 612, an outer insulation layer is deposited on the antenna to encase the antenna between the intermediate insulation layer and the outer insulation layer. The outer insulation layer may be inert and biocompatible, such as parylene.

The embodiments described herein provide one or more antennas on a housing of an IMD with less complexity than the conventional approach of stamping and forming metal antenna, positioning the antenna in place relative to the housing, and then welding the antenna to one or more conductors. The assembly method described herein of forming the antenna(s) in-situ on the housing may eliminate several steps of the conventional process and may also accommodate small IMD form factors, without sacrificing antenna performance.

Embodiments of the method of IMD assembly described herein may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference.

Additionally or alternatively, the IMD that is produced according to the method may be a leadless implantable medical device (LIMD). The LIMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the LIMD may be a leadless cardiac monitor (ICM) that includes one or more structural and/or functional aspects of the device(s) described in U.S. Patent Application having U.S. patent application Ser. No. 15/084,373, filed Mar. 29, 2016, entitled, "Method And System To Discriminate Rhythm Patterns In Cardiac Activity," which is expressly incorporated herein by reference.

Additionally or alternatively, the IMD that is produced according to the method may be a subcutaneous IMD that includes one or more structural and/or functional aspects of the device(s) described in U.S. application Ser. No. 15/973, 195, titled "Subcutaneous Implantation Medical Device With Multiple Parasternal-Anterior Electrodes" and filed May 7, 2018, and U.S. application Ser. No. 15/973,219, titled "Implantable Medical Systems And Methods Including Pulse Generators And Leads" filed May 7, 2018, U.S. application Ser. No. 15/973,249, titled "Single Site Implantation Methods For Medical Devices Having Multiple Leads", filed May 7, 2018, which are hereby incorporated by reference in their entireties. Further, one or more combinations of IMDs may be utilized from the above incorporated patents and applications in accordance with embodiments herein.

Embodiments may be implemented in connection with one or more passive implantable medical devices (PIMD). Non-limiting examples of PIMDs may include passive wireless sensors used by themselves, or incorporated into or used in conjunction with other implantable medical devices (IMDs) such as cardiac monitoring devices, pacemakers, cardioverters, cardiac rhythm management devices, defibrillators, neurostimulators, leadless monitoring devices, leadless pacemakers, replacement valves, shunts, grafts, drug elution devices, blood glucose monitoring systems, orthopedic implants, and the like. For example, the PIMD may include one or more structural and/or functional aspects of the device(s) described in U.S. Pat. No. 9,265,428 entitled "Implantable Wireless Sensor", U.S. Pat. No. 8,278,941 entitled "Strain Monitoring System and Apparatus", U.S. Pat. No. 8,026,729 entitled "System and Apparatus for In-Vivo Assessment of Relative Position of an Implant", U.S. Pat. No. 8,870,787 entitled "Ventricular Shunt System and Method", and U.S. Pat. No. 9,653,926 entitled "Physical Property Sensor with Active Electronic Circuit and Wireless Power and Data Transmission", which are all hereby incorporated by reference in their respective entireties.

All references, including publications, patent applications and patents, cited herein are hereby incorporated by reference to the same extent as if each reference were individually and specifically indicated to be incorporated by reference and were set forth in its entirety herein.

It should be clearly understood that the various arrangements and processes broadly described and illustrated with respect to the figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method for producing an implantable medical device (IMD), the method comprising:
forming a channel along a surface of a housing of the IMD, the channel formed to have a shape of an antenna design;
depositing a conductive material into the channel to at least partially fill the channel and adopt the shape of the channel, the conductive material forming an antenna of the IMD on the housing;

depositing an electrically insulative material on the surface of the housing to encase the antenna; and
electrically connecting the antenna to communication circuitry contained within the housing to facilitate wireless communication with at least one of a second IMD or an external device.

2. The method of claim 1, wherein the conductive material is deposited into the channel in multiple stacked layers during an additive manufacturing build process.

3. The method of claim 1, wherein the conductive material is deposited into the channel while the conductive material in a non-solid state and forms the antenna in-situ on the housing upon solidifying.

4. The method of claim 1, further comprising positioning at least a portion of a pin into a connection end of the channel prior to depositing the conductive material into the channel, the pin configured to be electrically connected to communication circuitry within the housing.

5. The method of claim 1, further comprising submitting the housing to a heat application after depositing the conductive material to harden the conductive material and form the antenna.

6. The method of claim 1, wherein the housing includes a main body that is electrically conductive and the method further comprises:
applying an intermediate insulation layer that surrounds the main body prior to depositing the conductive material into the channel such that the intermediate insulation layer is disposed between the conductive material and the main body, and
applying an outer insulation layer that surrounds the conductive material and the intermediate insulation layer to encase the antenna.

7. The method of claim 1, wherein the housing includes a cylindrical body and the channel is formed along an outer surface of the cylindrical body so that the antenna formed within the channel curves along at least one-fourth of a circumference of the cylindrical body.

8. The method of claim 1, wherein forming the channel along the surface of the housing comprises forming a primary portion and multiple secondary portions that branch off from the primary portion of the channel.

9. The method of claim 1, wherein the channel is a first channel, the antenna is a first antenna, and the method further comprises:
forming a second channel along the surface of the housing; and
depositing the conductive material into the second channel to at least partially fill the second channel and form a second antenna of the IMD on the housing,
wherein the second channel has one of (i) a different shape than the first channel along the surface of the housing for the second antenna to provide different antenna properties than the first antenna or (ii) a same shape as the first channel and is at least one of spaced apart from the first channel along a dimension of the housing or oriented to project in a different direction than the first channel.

10. A method for producing an implantable medical device (IMD), the method comprising:
forming a channel along a surface of a housing of the IMD, the channel formed to have a shape of an antenna design;
depositing a conductive material into the channel to at least partially fill the channel and adopt the shape of the channel, the conductive material forming an antenna of the IMD on the housing; and electrically connecting the antenna to communication circuitry contained within the housing to facilitate wireless communication with at least one of a second IMD or an external device, wherein the housing includes a header and a main body that contains a battery and an electronics module, and the method further comprises attaching the header to an end of the main body, wherein forming the channel along the surface of the housing comprises forming the channel along an outer surface of the main body.

11. An implantable medical device comprising:

a housing that contains a battery and an electronics module, the housing defining a channel along an outer surface of the housing, the channel extending from a connection hole, the channel having a shape of an antenna design;

an electrically insulative material deposited on the surface of the housing to encase the antenna;

a pin electrically connected to communication circuitry of the electronics module, a tip of the pin positioned at the connection hole; and an antenna disposed within the channel along the outer surface of the housing and adopting the shape of the channel, the antenna electrically connected to the pin and configured to facilitate wireless communication with and at least one of a second IMD or an external device.

12. The implantable medical device of claim 11, wherein the tip of the pin is embedded within a conductive material of the antenna.

13. The implantable medical device of claim 11, further comprising an outer insulation layer that encases the antenna.

14. The implantable medical device of claim 11, wherein a body of the housing that defines the outer surface is electrically conductive, and an intermediate insulation layer is disposed between the antenna and the body to electrically insulate the antenna from the body.

15. The implantable medical device of claim 11, wherein the channel defined along the outer surface of the housing has a primary portion and multiple secondary portions that branch off from the primary portion of the channel.

16. The implantable medical device of claim 11, wherein the housing includes a cylindrical body that defines the channel, and the antenna within the channel curves along at least one-fourth of a circumference of the cylindrical body.

* * * * *